(12) United States Patent
Fain et al.

(10) Patent No.: US 6,636,764 B1
(45) Date of Patent: Oct. 21, 2003

(54) SAFETY BACKUP IN ARRHYTHMIA DISCRIMINATION ALGORITHM

(75) Inventors: Eric S. Fain, Menlo Park, CA (US); Elisabeth Clem, Redwood City, CA (US); Lisa Malden, Sunny Isles, FL (US)

(73) Assignee: Pacesetter, Inc., Sunnyvale, CA (US)

( * ) Notice: Subject to any disclaimer, the term of this patent is extended or adjusted under 35 U.S.C. 154(b) by 124 days.

(21) Appl. No.: 09/991,471

(22) Filed: Nov. 16, 2001

Related U.S. Application Data

(60) Provisional application No. 60/253,667, filed on Nov. 28, 2000.

(51) Int. Cl.$^7$ .................................................. A61N 1/39
(52) U.S. Cl. ........................................................ 607/5
(58) Field of Search ................................. 607/4, 5, 14

(56) References Cited

U.S. PATENT DOCUMENTS

| 4,971,058 A | 11/1990 | Pless et al. ............ 128/419 PG |
| 5,107,850 A | 4/1992 | Olive .......................... 128/705 |
| 5,755,736 A | 5/1998 | Gillberg et al. ................. 607/4 |
| 5,913,878 A | 6/1999 | Hsung et al. ................... 607/5 |
| 6,430,435 B1 * | 8/2002 | Hsu et al. |
| 6,484,055 B1 * | 11/2002 | Marcovecchio |

* cited by examiner

Primary Examiner—Scott M. Getzow
(74) Attorney, Agent, or Firm—Steven M. Mitchell

(57) ABSTRACT

In an arrhythmia discrimination algorithm a timer is used to trigger the delivery of therapy when no diagnosis is made within a defined time during a tachycardia episode. Where one or more rhythm discriminators or qualifiers such as morphology, sudden onset, interval stability and AV association is enabled, the timer starts as soon as a ventricular interval or interval average is faster than a programmed maximum time to diagnosis (MTD) cutoff. If the timer times out before the algorithm diagnoses a particular rhythm, a programmed therapy is delivered. In the preferred embodiment, the therapy that is triggered is a function of the most recent detected ventricular rate and the programmed MTD therapy.

18 Claims, 3 Drawing Sheets

SAFETY BACKUP IN ARRHYTHMIA DISCRIMINATION ALGORITHM

This application claims the benefit of U.S. Provisional Application No. 60/253,667, filed Nov. 28, 2000.

FIELD OF THE INVENTION

The present invention relates generally to implantable pulse generators for treating cardiac arrhythmias, and more specifically to a safety timeout for use with a method for discrimination between supraventricular and ventricular tachyarrhythmias.

BACKGROUND OF THE INVENTION

One of the most frequent causes of follow-ups for patients with an implantable cardioverter-defibrillator (ICD) is inappropriate therapy. Between 15% and 30% of ICD patients receive inappropriate therapies because of supra-ventricular tachycardias (SVT). Single chamber defibrillators have algorithms such as morphology discrimination, sudden onset and interval stability that can be used to differentiate between ventricular tachycardias (VT) versus those that originate supra-ventricularly, i.e., in the atria. These algorithms have provided increased specificity for SVTs while still maintaining a high level of sensitivity to VT, but inappropriate therapies can still occur.

With the advent of dual-chamber defibrillators that sense both in the atrium and ventricle, atrial rate has been used to aid in the identification of VTs and SVTs. This has further increased the specificity for SVTs, but relying solely on the relationships between the rates of atrial and ventricular sensed events can result in erroneous classifications. Existing dual-chamber ICDs have exhibited difficulty in diagnosing certain rhythms correctly such as sinus tachycardia (tach), SVTs with 1:1 ventricular conduction, and VT with 1:1 retrograde conduction. VT with 1:1 retrograde conduction may look like sinus tach if the retrograde conduction interval is quite long. Conversely, sinus tach with first degree AV block can be classified by some schemes as a retrograde VT. Ventricular tachycardia during an atrial tachycardia has also been erroneously detected as SVT. Various diagnostic qualifiers can be implemented for improved discrimination of SVT from VT where the atrial and ventricular rates are the same or when the atrial rate is greater than the ventricular rate. However, they present the possible problem of extending the time required before a diagnosis is made and therapy is delivered. This is particularly problematic where a ventricular tachycardia is hemodynamically compromising or may degrade to ventricular fibrillation. It is desirable to provide a safety backup in the discrimination algorithm to ensure therapy is delivered where appropriate.

SUMMARY OF THE INVENTION

The present invention provides a timer that is used to trigger the delivery of therapy when no diagnosis is made within a defined time during a tachycardia episode. In a diagnostic algorithm where one or more rhythm discriminators or qualifiers such as morphology, sudden onset, interval stability and AV association is enabled, the timer starts as soon as a ventricular interval or interval average is faster than a programmed maximum time to diagnosis (MTD) cutoff. This trigger may be further limited to an SVT overlap zone beyond which the rapid ventricular rate is automatically considered a VT. If the timer times out before the algorithm diagnoses a particular rhythm, a prescribed therapy is delivered. In the preferred embodiment, the therapy that is triggered is a function of the most recent detected ventricular rate and the programmed MTD therapy.

In a preferred embodiment of the invention, a rate of ventricular contractions is sensed from a patient's heart. If the ventricular rate exceeds a tachycardia threshold but is less than an SVT overlap zone upper limit, an episode timer is started. The sensed heart rhythm is analyzed using at least one arrhythmia qualifier to determine if a ventricular tachycardia should be diagnosed. If the presence or absence of a ventricular tachycardia is not diagnosed by the time the episode timer reaches an MTD cutoff, a programmed therapy is delivered.

BRIEF DESCRIPTION OF THE DRAWINGS

The various features and advantages of the present invention may be more readily understood with reference to the following detailed description taken in conjunction with the accompanying drawings in which.

DETAILED DESCRIPTION OF THE INVENTION

Figure 1:
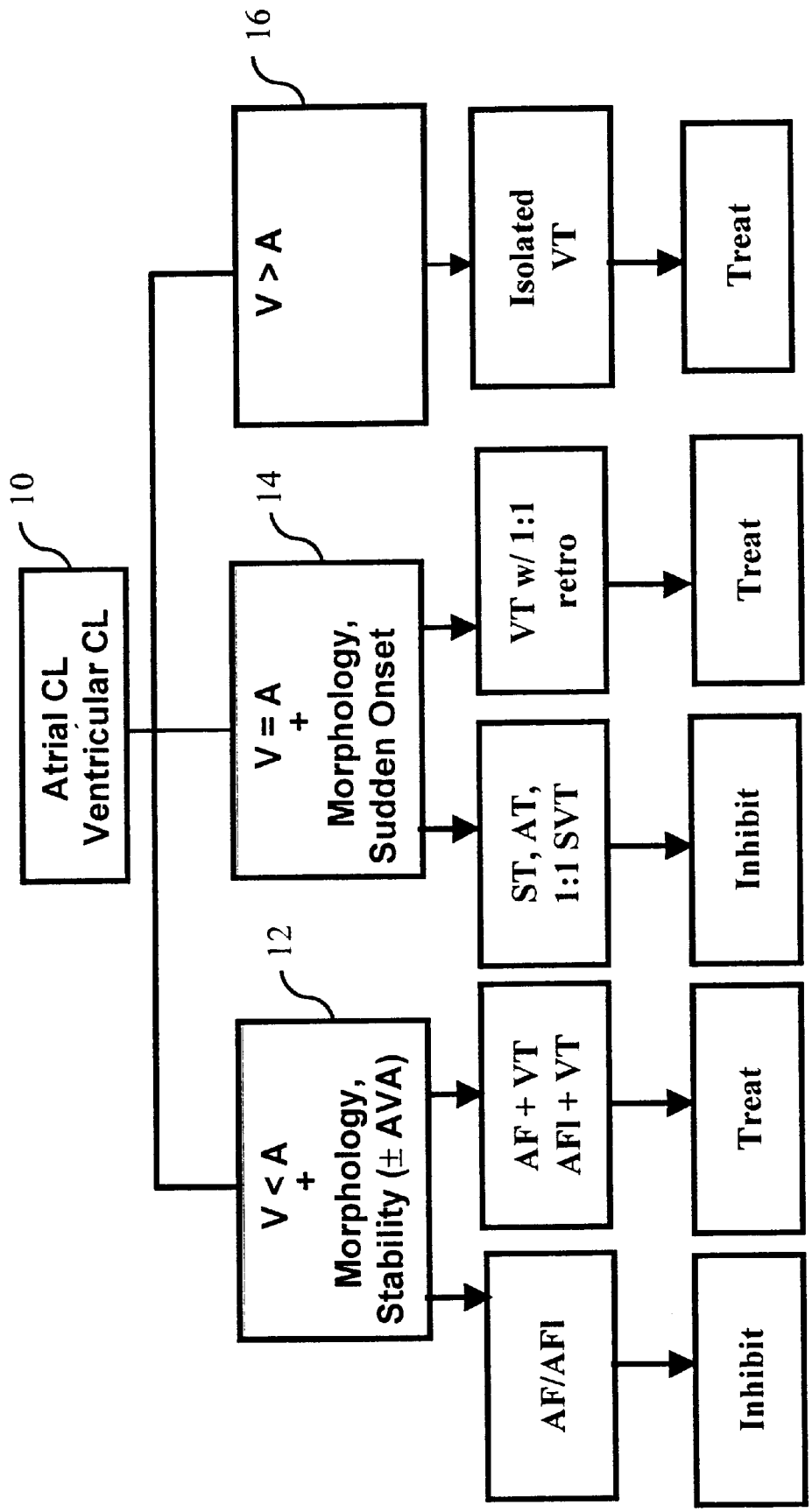
FIG. 1 illustrates a tachyarrhythmia discrimination algorithm within which the invention may be implemented.

Referring now to FIG. 1, a rate branch algorithm within which the Maximum Time to Diagnosis (MTD) algorithm may be implemented is disclosed. The MTD algorithm of the invention can be used in the context of a rate branch algorithm or could be used with other discrimination algorithms where identification of a possible ventricular tachycardia (VT) in the presence of a supraventricular tachycardia (SVT) is desirable and arrhythmia detection qualifiers may delay diagnosis of the rhythm. While described in the context of a dual chamber ICD, the invention can alternatively be implemented in a single chamber or other multiple chamber device. Dual-chamber arrhythmia sensing illustrated in FIG. 1 is implemented with a rate branch discriminator. At step 10 the device detects a tachyarrhythmia in a rate overlap zone based on atrial and ventricular cycle lengths. The relationship between the atrial and ventricular rates is assessed. By comparing the median atrial rate with the median ventricular rate within a recent history of intervals, the pulse generator classifies the rhythm into the V<A (box 12), V=A (box 14) or V>A (box 16) Rate Branch.

When the ventricular rate is less than the atrial rate, the rhythm is classified as V<A. Morphology Discrimination and Interval Stability qualifiers are available in this branch to further qualify the rhythm. These SVT discriminators, described in greater detail below and in U.S. Pat. Nos. 5,779,645 and 5,941,831, respectively, which patents are incorporated herein by reference, can help distinguish VT from atrial fibrillation or atrial flutter but can also potentially impose a prolonged delay prior to rhythm diagnosis.

When the ventricular rate is essentially the same as the atrial rate (within a certain tolerance), the rhythm is classified as V=A. Morphology Discrimination and Sudden Onset qualifiers are available in this branch to further qualify the rhythm. These SVT discriminators can help distinguish 1:1 retrograde VT from sinus tachycardia. In an ICD of the preferred embodiment, the V=A Rate Branch 14 can be programmed On or Off. When the V=A Rate Branch is Off and the ventricular rate is essentially the same as the atrial rate, the pulse generator would reclassify the rhythm into the V>A Rate Branch 16 causing VT to be diagnosed. This may be desirable if the maximum achievable sinus tach rate for the patient does not cross over into the tachycardia zones.

When the ventricular rate is greater than the atrial rate in Rate Branch 16, the rhythm is classified as V>A. No SVT discrimination criteria are used to qualify the diagnosis. Diagnosis of VT occurs immediately and the device initiates therapy. It is worth noting that in the device of the preferred embodiment, if the detected ventricular rate exceeds a programmed fibrillation threshold, the rate branch algorithm is not entered and the device triggers fibrillation therapy.

As mentioned above, Morphology is one qualifier used to discriminate VT from SVT. Since SVTs originate in the atria and follow the normal conduction pathway to the ventricles (via the AV node), the shape (morphology) of the arrhythmia's complexes as recorded from the bipolar sensing electrodes in the right ventricular apex should be similar to the patient's sinus complexes and different from the VT complexes originating in the ventricle. The Morphology qualifier can, therefore, help distinguish SVTs such as sinus tach, atrial fibrillation and atrial flutter from VT. Thus, the Morphology qualifier is available in Ventricular Only arrhythmia sensing and in both the V<A and V=A rate branches 12, 14 when configured to dual-chamber arrhythmia sensing.

The morphology algorithm uses attributes such as the number, amplitude, polarity, and area of up to five peaks in the intrinsic ventricular complex. The complexes are compared to a sinus template and a percent match between 0 and 100% is generated. The more similar the test complex is to the template, the higher the score. Once the onset of an episode is detected, the device scores all intrinsic events until diagnosis of an arrhythmia occurs. If the score for a complex is greater than or equal to the programmable % Match threshold, the complex is considered to match the template. Otherwise, the complex does not match the template. When a detection occurs, a programmable window of the most recent scores is examined and Morphology indicates SVT if the number of matches meets or exceeds a programmable threshold. If the number of matches is less than the programmable threshold, Morphology indicates VT.

The morphology template that is used during the episode can either be acquired and validated by the physician, or it may be acquired automatically by the device. In the St. Jude Medical Photon DR device in which the Rate Branch algorithm is implemented, an Automatic Template Update algorithm periodically evaluates the current template to determine if it is representative of the patient's intrinsic rhythm, and if necessary, acquires a new template. This feature reacts to changes in the patient's morphology that can occur due to lead maturation or changes in the patient's medication. The Automatic Template Update frequency may be programmable for example from 8 hours to 30 days. When the Automatic Template Update timer expires, the current template is evaluated to see if it is representative of the patient's intrinsic rhythm. If it is not representative of the patient's intrinsic rhythm, then a new template is acquired. If the new template is representative of the patient's intrinsic rhythm, the new template becomes the active template and will be used during episodes. If the new template is not representative of the patient's intrinsic rhythm, the current active template will be retained and the Automatic Template Update timer will be postponed to 8 hours.

The Sudden Onset discriminator can help distinguish between VT and sinus tachycardia in patients whose maximum sinus rates can exceed the rates of their slowest ventricular tachyarrhythmias ("rate overlap"). Typically, sinus tachycardia has a gradual rate of onset, while ventricular tachycardia has a more abrupt onset. The Sudden Onset qualifier is preferably implemented in Ventricular Only arrhythmia sensing and in the V=A rate branch when configured to dual-chamber arrhythmia sensing.

Once tachycardia intervals are detected, the device compares the average interval to previous interval averages to determine whether the difference (either absolute or percent change) is large enough to satisfy the Sudden Onset criterion. Since average intervals are used for the comparison, a single long interval during a gradual increase in rate may (appropriately) result in failure to satisfy the Sudden Onset criterion. Alternatively, after an abrupt change in cycle length greater than the selected Sudden Onset Delta, a single long interval amid several short intervals will probably still allow the Sudden Onset criterion to be satisfied. The Sudden Onset criterion is met when the delta between averages is greater than or equal to the programmed Sudden Onset Delta. The shorter the programmed sudden onset delta, the more likely it is that a rhythm will be classified as VT.

The Interval Stability discriminator can help distinguish between atrial fibrillation (AF) and VT, because atrial fibrillation often shows rate variability in conduction into the ventricles and VT typically has little rate variability. The Interval Stability qualifier is available in Ventricular Only arrhythmia sensing and in the V<A rate branch when configured to dual-chamber arrhythmia sensing. The Interval Stability qualifier is evaluated upon detection of a tachycardia. The measured Interval Stability Delta is the difference between the second longest and the second shortest ventricular intervals in a recent group of intervals defined by a programmable window size. If the measured delta is equal to or greater than the programmed delta, the discriminator indicates SVT. The longer the programmed stability delta, the more likely it is that a rhythm will be classified as VT.

AV Association (AVA) is a secondary qualifier that may be used in conjunction with Interval Stability to discriminate atrial flutter (AFl) from VT. Atrial Flutter often results in stable ventricular intervals and so can cause Interval Stability to indicate VT. If Interval Stability is On with AVA and Interval Stability indicates VT, the measured AVA Delta is examined. A valid conduction interval (AV interval) is measured from each ventricular sensed event to its preceding atrial event. The AVA Delta is then calculated as the difference between the second longest AV interval and the second shortest AV interval in a recent group of intervals. If the measured AVA Delta is less than a programmable AVA threshold, the AV intervals are considered stable and SVT is indicated. If the measured AVA Delta is greater than or equal to a programmable AVA threshold, the AV intervals are considered unstable and VT is indicated.

The ICD of the preferred embodiment can be configured to detect zero, one or two tachycardia zones in addition to a fibrillation zone based on ventricular rate. The device is continuously binning intervals as sinus, tachycardia or fibrillation using a combination of the current ventricular interval and a running ventricular average composed of the last four ventricular intervals. When a programmable number of intervals have been binned in one of the rate zones, a detection is said to have occurred. If a sinus detection occurs, sinus is diagnosed immediately and the counts for the tachycardia and fibrillation zones are cleared and if an episode is currently ongoing, the episode is terminated. If a fibrillation detection occurs, fibrillation is also diagnosed immediately and the device begins charging immediately for the first programmed fibrillation therapy. If a tachycardia detection occurs, all applicable discriminators must be satisfied before a VT diagnosis can occur. Otherwise, the diagnosis will be inhibited and the device will withhold therapy. If the discriminators inhibit diagnosis of VT, the tachycardia counts will be reset to a programmable value and the device will continue to monitor the arrhythmia. The discriminators will be re-examined if another detection occurs.

Figure 2:
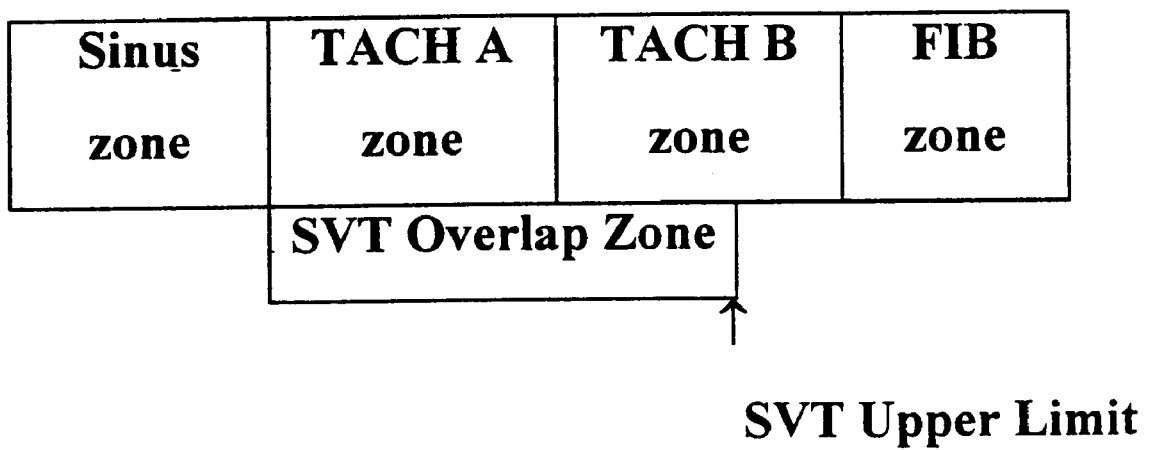
FIG. 2 illustrates the two tachycardia zone configuration of an arrhythmia detection algorithm according to the invention.

When detection in one of the tachycardia rate zones has occurred, the device then checks whether the ventricular interval average at the time of detection is within the SVT Overlap zone. As illustrated in FIG. 2, the SVT Overlap zone begins at the slowest tachycardia cutoff and ends at the programmable SVT Upper Limit cutoff. The SVT Overlap may cover some or all of the programmed tachycardia detection zones, but may not extend into the fibrillation zone. If the ventricular interval average is not within the SVT Overlap zone, a VT diagnosis occurs immediately and the device will deliver the first programmed therapy in the appropriate rate zone.

When the device is programmed to Dual-Chamber Arrhythmia Sensing, the Rate Branch qualifier then compares the ventricular and atrial rates and classifies the rhythm as V>A (Rate Branch 16), V=A (Rate Branch 14) or V<A (Rate Branch 12). If the ventricular rate is greater than the atrial rate (V>A), a VT diagnosis occurs immediately and the device will deliver the first programmed therapy in the appropriate rate zone. If the rhythm is classified as V<A or V=A, the SVT discriminators in that branch that are programmed to On or Passive are evaluated. If only one SVT discriminator is programmed to On in a branch, the result of that qualifier will either cause or inhibit a VT diagnosis. If no qualifiers are programmed to On in the branch, then Rate Branch is used as the qualifier and diagnosis of VT is inhibited because the ventricular rate is not greater than the atrial rate. It is noted that this functions differently than when the device is configured to Ventricular Only Arrhythmia Sensing.

If more than one SVT discriminator is programmed On in a branch, the Tachycardia Diagnosis Criteria must be programmed as in Dual-chamber Arrhythmia Sensing. If two SVT discriminators are programmed On in a branch, the Tachycardia Diagnosis Criteria must be programmed to "If Any" or "If All". "If Any" requires that at least one of the discriminators indicate VT in order to cause a VT diagnosis. Otherwise, diagnosis will be inhibited and the tachycardia counters will be reset. "If All" requires that both of the discriminators indicate VT in order to cause a VT diagnosis. If all three discriminators are programmed to On, the options are "If Any", "2 of 3", or "If All".

The SVT discriminators are re-evaluated on every detection where the interval average falls in the SVT Overlap zone until a VT diagnosis occurs in an episode. Once a VT diagnosis has occurred during the episode, the SVT discriminators no longer apply.

When the device is programmed to Ventricular Only Arrhythmia Sensing, i.e., Single-Chamber discrimination, the SVT discriminators are immediately evaluated if the arrhythmia falls in the SVT Overlap zone. If no qualifiers are programmed to On, VT is diagnosed immediately and the device will deliver the first programmed therapy in the appropriate rate zone because there is no information about the atrial rate. If only one SVT discriminator is programmed to On in a branch, the result of that qualifier will either cause or inhibit a VT diagnosis.

Figure 3:
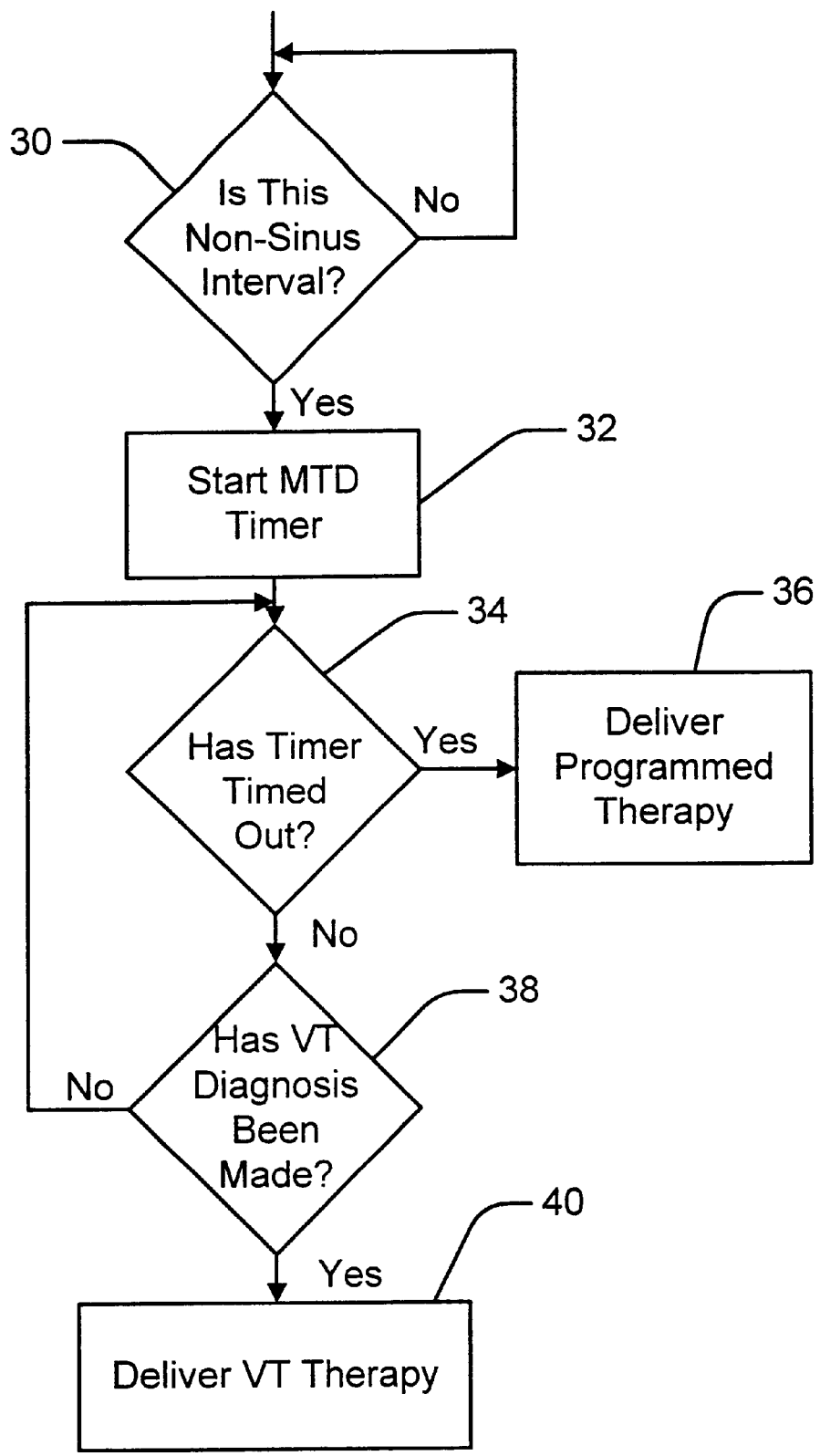
FIG. 3 is a flow chart illustrating the steps of the method of the invention.

Referring now to FIG. 3, the Maximum Time to Diagnosis (MTD) feature of the invention will be described. To prevent inappropriate inhibition of therapy for a long period of time, a programmable MTD timer designed to allow the SVT discriminators to inhibit therapy for a programmable length of time is provided. The MTD timer is started at step 32 when it is determined at step 30 that the first non-sinus interval is binned during an episode. If a diagnosis has not occurred before the MTD timer elapses at step 34, MTD will override the SVT discriminators and begin delivering programmed therapy at 36. If VT is diagnosed at step 38 before the timer times out, VT therapy is delivered at step 40. If no diagnosis has been made or a SVT is diagnosed, therapy is inhibited and he episode continues for as long as the ventricular rate falls in the SVT overlap zone. If the ventricular rate accelerates beyond the SVT upper limit, then VT or ventricular fibrillation (VF), as appropriate for the rate is diagnosed. If the ventricular rate falls below the lower tach threshold, sinus is diagnosed and the episode is terminated.

The MTD Therapy can be programmed to deliver either the first Tach therapy or the first Fib therapy. If the MTD Therapy is set to Tach therapy and the device is configured with two tachycardia zones, the device will deliver therapy when the MTD timer expires based on the cycle length for the last inhibited diagnosis.

Although presently preferred embodiments of the present invention have been described in detail hereinabove, it should be clearly understood that many variations and/or modifications of the basic inventive concepts herein taught, which may appear to those skilled in the pertinent art, will still fall within the spirit and scope of the present invention, as defined in the appended claims.

What is claimed is:

1. A method for use in a cardiac therapy device for discriminating between a supraventricular tachycardia and a ventricular tachycardia comprising the steps of:

sensing a cardiac rhythm indicative of cardiac function of a patient's heart;

detecting a ventricular rate;

determining if the ventricular rate is within a ventricular tachycardia rate zone;

starting a timer following detection of a rate in the tachycardia rate zone;

if the ventricular rate is in the ventricular tachycardia rate zone, applying at least one rhythm qualifier to the sensed cardiac rhythm to diagnose whether the cardiac rhythm is a ventricular tachycardia or a supraventricular tachycardia; and if a diagnosis of the cardiac rhythm is not determined based on the at least one rhythm qualifier within a predetermined time as measured by the timer, delivering a programmed therapy to the heart.

2. The method of claim 1 wherein said step of sensing a cardiac rhythm includes sensing an electrogram signal from a ventricle of a patient's heart and an electrogram signal from an atrium of the patient's heart.

3. The method of claim 2 and further including the step of detecting an atrial rate.

4. The method of claim 1 and further including the step of defining an SVT rate overlap zone and wherein said step of determining if the ventricular rate is within a ventricular tachycardia rate zone includes the step of determining if the ventricular rate is within the SVT rate overlap zone.

5. The method of claim 1 wherein said step of starting a timer comprises starting the timer with the detection of a first non-sinus interval.

6. The method of claim 1 wherein said step of starting a timer comprises starting the timer with the detection of a first non-sinus interval average.

7. The method of claim 1 wherein said step of applying at least one rhythm qualifier includes applying a morphology discrimination qualifier.

8. The method of claim 1 wherein said step of applying at least one rhythm qualifier includes applying an interval stability qualifier.

9. The method of claim 1 wherein said step of applying at least one rhythm qualifier includes applying an interval stability with AV association qualifier.

10. The method of claim 1 wherein said step of applying at least one rhythm qualifier includes applying a sudden onset qualifier.

11. The method of claim 1 wherein said step of applying at least one rhythm qualifier includes applying at least two of a morphology discrimination qualifier, an interval stability or interval stability with AV association qualifier, and a sudden onset qualifier.

12. The method of claim 1 wherein the therapy delivered is a function of the most recent detected ventricular rate.

13. An arrhythmia discrimination algorithm for analyzing a cardiac rhythm in an implantable cardioverter defibrillator comprising the steps of:

determining a ventricular rate and an atrial rate for a patient's heart;

if the ventricular rate falls in a programmed tachycardia rate zone and is greater than the atrial rate by more than a prescribed delta, diagnosing ventricular tachycardia and delivering a programmed therapy;

if the ventricular rate falls in the programmed tachycardia rate zone and is less than or substantially equal to the atrial rate then further analyzing the rhythm using one or more rhythm qualifiers to diagnose a ventricular tachycardia;

starting a timer following detection of a rate in the tachycardia rate zone;

if the ventricular rate is in the tachycardia rate zone, applying at least one rhythm qualifier to the sensed cardiac rhythm to diagnose whether the cardiac rhythm is a ventricular tachycardia or a supraventricular tachycardia; and if a diagnosis of the cardiac rhythm is not determined based on the at least one rhythm qualifier within a predetermined time as measured by the timer, delivering a programmed therapy to the heart.

14. The method of claim 13 and further including the step of defining an SVT rate overlap zone and wherein said step of determining if the ventricular rate is within a tachycardia rate zone includes the step of determining if the ventricular rate is within the SVT rate overlap zone.

15. The method of claim 13 wherein said step of starting a timer comprises starting the timer with the detection of a first non-sinus interval.

16. The method of claim 13 wherein said step of starting a timer comprises starting the timer with the detection of a first non-sinus interval average.

17. The method of claim 13 wherein said step of applying at least one rhythm qualifier includes applying a qualifier from among morphology discrimination, interval stability, interval stability with AV association and sudden onset.

18. The method of claim 13 wherein the therapy delivered is a function of the most recent detected ventricular rate.

* * * * *